United States Patent [19]

Nestegard

[11] Patent Number: 4,894,060
[45] Date of Patent: Jan. 16, 1990

[54] DISPOSABLE DIAPER WITH IMPROVED HOOK FASTENER PORTION

[75] Inventor: Susan K. Nestegard, Woodbury, Minn.

[73] Assignee: Minnesota Mining and Manufacturing Company, Saint Paul, Minn.

[21] Appl. No.: 142,551

[22] Filed: Jan. 11, 1988

[51] Int. Cl.$^4$ .............................................. A61F 13/16
[52] U.S. Cl. ............................ 604/391; 128/DIG. 15; 24/442
[58] Field of Search ............... 128/DIG. 15; 604/391; 24/306, 442–452; 2/DIG. 6

[56] References Cited

U.S. PATENT DOCUMENTS

| | | | |
|---|---|---|---|
| 3,138,841 | 6/1964 | Naimer | 24/442 |
| 3,147,528 | 9/1964 | Erb | 24/452 |
| 3,196,511 | 7/1965 | Kintner | 24/442 |
| 3,266,113 | 8/1966 | Flanagan, Jr. | 24/204 |
| 3,557,413 | 1/1971 | Engle | 24/201 |
| 3,900,682 | 8/1975 | Uraya et al. | 24/442 |
| 4,001,366 | 1/1977 | Brumilk | 264/147 |
| 4,056,593 | 11/1977 | de Navas Albareda | 264/145 |
| 4,169,303 | 10/1979 | Lemelson | 24/442 |
| 4,189,809 | 2/1980 | Sotos | 24/204 |
| 4,290,174 | 9/1981 | Kalleberg | 24/442 |
| 4,290,831 | 9/1981 | Kalleberg | 156/72 |
| 4,322,875 | 4/1982 | Brown et al. | 24/442 |
| 4,541,154 | 9/1985 | Ho et al. | 24/442 |
| 4,553,550 | 11/1985 | Hattori | 128/505 |
| 4,704,117 | 11/1987 | Mitchell | 607/391 |

FOREIGN PATENT DOCUMENTS

| | | |
|---|---|---|
| 0211564 | 2/1987 | European Pat. Off. |
| 0276970 | 3/1988 | European Pat. Off. |
| 2082591 | 12/1971 | France |
| 2602285 | 2/1988 | France |

*Primary Examiner*—Max Hindenburg
*Assistant Examiner*—K. M. Reichle
*Attorney, Agent, or Firm*—Donald M. Sell; Walter N. Kirn; William L. Huebsch

[57] ABSTRACT

A hook fastener portion including a thin strong flexible plate like backing and a multiplicity of resiliently flexible spaced hook members projecting at generally a right angle from an upper surface of the backing. The hook members each comprise a stem portion attached at one end to the backing and a head portion at the end of the stem portion opposite the backing that is flush with the stem portion on two opposite sides, projects past the stem portion on two opposite sides, and has a rounded surface opposite the stem portion to help the head portion enter between loops in a loop fastener portion. The hook members are more easily and firmly engaged with many types of loop fastener portions than the hook members on known commercially available hook fastener portions, in large part because they are very small compared to them, and the hook portions do not have an abrasive feel when contacted by a persons skin.

13 Claims, 2 Drawing Sheets

DISPOSABLE DIAPER WITH IMPROVED HOOK FASTENER PORTION

TECHNICAL FIELD

The present invention concerns hook fastener portions of hook and loop fasteners that are used on inexpensive or disposable garments such as diapers.

BACKGROUND OF THE INVENTION

Various fasteners have been used on inexpensive or disposable garments such as diapers, including lengths of pressure-sensitive adhesive coated tape, snaps, and hook and loop fasteners.

Of these, lengths of pressure-sensitive adhesive coated tape are presently most widely used as the fasteners for disposable diapers, however the presence of relatively small amounts of contaminants such as talcum powder or baby oil either on the pressure-sensitive adhesive or on the portion of the garment to which the pressure-sensitive adhesive is to be adhered by the user can reduce the reliability of the fastener.

The use of hook and loop fasteners on inexpensive or disposable garments such as diapers substantially overcomes this problem of reduced fastener reliability due to contaminants such as talcum powder or baby oil, however, many hook and loop fasteners are too expensive to be economically used on disposable diapers, particularly since the loop portion must be very large to provide a variety of fastening locations for the hook portion to fit various sizes of babies to which the diapers may be attached. Thus, inexpensive portions for hook and loop fasteners are being developed that can securely close the diaper and allow a limited number (e.g., 10) openings and closings of the fastener without seriously degrading it, and are sufficiently inexpensive that they can economically be used on a disposable diaper or similar garment. Included in such development as is described in U.S. Pat. application No. 126,746 filed Nov. 30, 1987, are loop fastener portions having loops projecting from one surface that are formed by stitching through a backing, sonically welding portions of fibers to one face of a backing layer, or by providing a nonwoven fibrous layer that provides such loops. Typically, such inexpensive loop fastener portions provide per unit area fewer, smaller loops with less height compared to most commercially available woven or knitted loop fastener portions (e.g., the loop fastener portion commercially available as Style No. 19149 nylon 66 loop material from Guilford Mills, Inc., Greensboro, NC). Thus, the level of engagement with such inexpensive loop fastener portions by commercially available hook fastener portions, whether of the type having monofilament hooks projecting from a woven or knit backing formed by cutting monofilament loops along one side (e.g., see U.S. Pat. No. 3,027,566) or of the type having monofilament stems with mushroom shaped heads on their distal ends and projecting from a backing that may be woven, knit or a unitary layer in which the stems are embedded (e.g., see U.S. Pat. Nos. 3,270,408 and 4,290,832), or of the type having unitary backings and projecting hook members molded together or formed by extrusion techniques, is not as good as the level of engagement those commercially available hook fastener portions make with the more costly woven or knitted loop fastener portions described above. A hook fastener portion of the type having projecting monofilament or molded stems with mushroom shaped heads on their distal ends will not make good engagement with such inexpensive loop fastener portions because for good engagement with such a mushroom shaped head a loop must be sufficiently long so that it can wrap almost completely around the stem under the head. Hook fastener portions of types having monofilament hooks projecting from a woven or knit backing formed by cutting monofilament loops along one side can engage with such inexpensive loop fastener portions better than stems with mushroom shaped heads, however the monofilament hooks are so flexible that they do not provide the desired level of shear strength when engaged with such inexpensive loop fastener portions. Hook fastener portions of the type having unitary backings and projecting hook members molded together or formed by extrusion techniques (which are the least expensive and thus from that standpoint are most suitable for use on disposable garments such as diapers) have greater shear strength than the monofilament hooks, but are too large to easily enter between the random loops of nonwoven inexpensive loop fastener portions Additionally, known hook fastener portions having unitary backings and projecting hook members made by molding or extrusion techniques are rigid as well as being quite large and therefore have a very abrasive feel when their projecting hook members are pressed against a person's skin so that they could cause concern among mothers or other users that inadvertent contact between such projecting hook members and the skin of a person, such as a baby, could cause discomfort or injury.

DISCLOSURE OF THE INVENTION

The present invention provides a hook fastener portion particularly adapted to mate with inexpensive loop fastener portions of the type described above that are formed by stitching through a backing, sonically welding portions of fibers to one face of a backing layer, or by forming a nonwoven fibrous layer, which hook fastener portion is both less expensive to form and can provide more complete and effective engagement with such inexpensive loop fasteners than the commercially available hook fastener portions described above.

According to the present invention there is provided a unitary polymeric hook fastener portion comprising a thin strong flexible plate like backing, and a multiplicity of resiliently flexible spaced hook members projecting at generally a right angle from the upper surface of the backing. The hook members each comprise a stem portion attached at one end to the backing, and a head portion at the end of the stem portion opposite the backing. The head portion projects past the stem portion on at least one of two opposite sides, and has a rounded surface opposite the stem portion to help the head portion enter between loops in a loop fastener portion. The hook members are more easily and firmly engaged with many types of loop fastener portions than the hook members on known commercially available hook fastener portions, in large part because their head portions are very small in cross section compared to head portions on the hook members of those commercially available hook fastener portions, and thus more easily penetrate into a loop structure. Specifically, the hook members each have a height dimension from the upper surface of the backing of less than 1.5 millimeter (0.06 inch) and preferably from about 0.08 to 0.11 centimeter (0.03 to 0.045 inch). The stem and head portions each have generally the same thickness dimension of less than 0.046 centimeter (0.018 inch) and preferably in the range of 0.020 to 0.028 centimeter (0.008 to 0.012 inch) in a first direction parallel to the surfaces of the backing. The stem portions each have a width dimension in the range of 0.018 to 0.03 centimeter (0.007 to 0.012 inch) in a second direction generally at a right angle to the first direction and parallel to the surfaces of the backing, and the head portions each have a width dimension in the second direction that is between 0.007 and 0.038 centimeter (0.003 and 0.015 inch) greater than the width dimension of the stem portion and a total width of less than 0.1 centimeter and preferably in the range of 0.04 to 0.065 centimeter (0.016 to 0.026 inch). Hook members of this small size have been found to easily penetrate between and engage the loops on the inexpensive types of loop fastener portions described above, but individually have little holding power so that the fastener portion includes at least 45, and preferably 70 to 100 per square centimeter (at least 300 and preferably 450 to 645 hook members per square inch) of the spaced hook members projecting from the upper surface of the backing to provide the required holding power, while the total cross sectional area occupied by the head portions in a plane parallel to the upper surface is less than 32 percent and preferably in the range of 5 to 15 percent of the area of the upper surface to retain the ease of engagement of the large number of projecting hook members with the loop fastener portion.

Suitable polymeric materials from which the hook fastener portion can be made include thermoplastic resins comprising polyolefins, e.g. polypropylene and polyethylene, polyvinyl chloride, polystyrene, nylons, polyester such as polyethylene terephthalate and the like and copolymers and blends thereof. Preferably the resin is a polypropylene/polyethylene copolymer or a blend of polypropylene with an ethylene-vinyl acetate block copolymer or a styrene-ethylene-butylene-styrene block copolymer.

Whatever polymeric material is used, the elastic modulus of the hook members should preferably be within the range from 100 to 500 megaPascals, as measured in said second direction (i.e., the direction the parts of the head portion project over the stem portion) according to ASTM D 882.80a, which measurement generally comprises measuring the initial slope of the stress strain curve from a tensile test of the material. Hook members with an elastic modulus in that range exhibit an excellent ability to initially engage loop structures of the type described above, and to resist shear and peel forces tending to separate them from the loop fastener portion once they are engaged. This combination of properties is believed to be due to the ability of the hook members to resiliently bend to move between loops during engagement, and to resiliently bend when they are pulled out of engagement with the loops which resilient bending minimizes breaking of both the small hook members and the loops, and thus prolongs the useful life and esthetics of both the hook fastener portion and the loop fastener portion with which it is mated.

The backing of the hook fastener portion must be thick enough to afford attaching it to a substrate by a desired means such as sonic welding, heat bonding, sewing or adhesives including pressure sensitive or hot melt adhesives, and to firmly anchor the stems and provide resistance to tearing when the fastener is peeled open, but when it is used on a disposable garment, should not be so thick that it is stiffer than necessary. The optimum thickness will vary depending upon the resin from which the hook fastener portion is made, but will generally be between 0.05 millimeter and 0.4 millimeters, and is preferably about 0.15 millimeters for the polyolefin resins. A plate like backing provides an advantage over a woven backing when it is adhered to a substrate in that such adhesion requires less adhesive.

Hook fastener portions having the number of hook portions per unit area of the size and made of the polymeric material indicated above have found to have a very smooth and non abrasive feel when the hook portions are pressed against a persons skin, which is desirable so that the hook portions will not cause discomfort or injury to the skin of a person with which inadvertent contact with the hook portions is made.

The hook fastener portion is made by an adaptation of a known method of making hook fastener portions described in U.S. Pat. Nos. 3,266,113; 3,557,413; 4,001,366; 4,056,593; and 4,189,809, which method generally includes extruding a thermoplastic resin through a die shaped to form a base layer and spaced ridges projecting above an upper surface of the base layer that have the cross sectional shape of the hook portions to be formed, transversely cutting the ridges at spaced locations along their length to form discrete portions of the ridges, and stretching the backing layer to separate those portions of the ridges which are then the spaced hook portions.

BRIEF DESCRIPTION OF DRAWING

The present invention will be further described with reference to the accompanying drawings wherein like reference numerals refer to like parts in the several views, and wherein.

DESCRIPTION OF THE PREFERRED EMBODIMENTS

Figure 1:
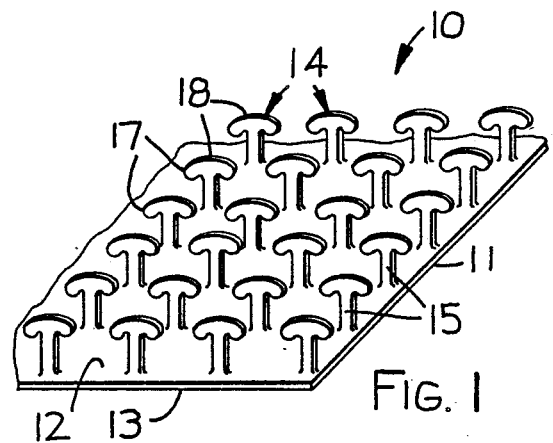
FIG. 1 is an enlarged perspective view of a hook fastener portion according to the present invention.

Referring now to the drawing, there is shown in FIG. 1 a unitary polymeric hook fastener portion according to the present invention generally designated by the reference numeral 10.

Figure 2:
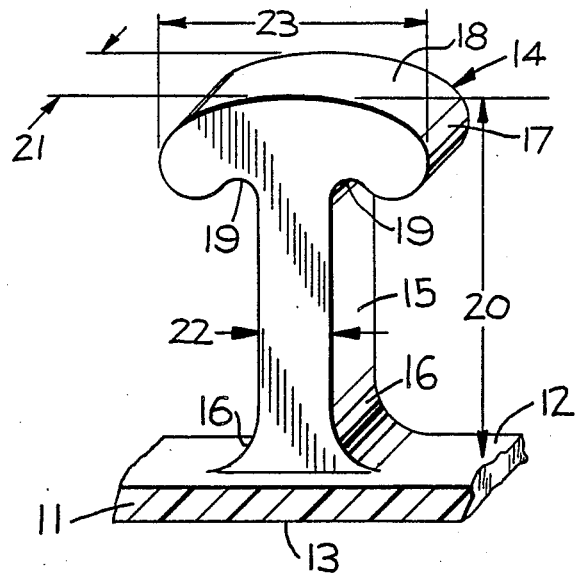
FIG. 2 is a much enlarged fragmentary perspective view of one hook member in the hook fastener portion of FIG. 1.

The hook fastener portion 10 comprises a thin strong flexible plate like backing 11 having generally planar and parallel upper and lower major surfaces 12 and 13, and a multiplicity of resiliently flexible spaced hook members 14 projecting at generally a right angle from the upper surface 12 of the backing 11. As is best seen in FIG. 2, the hook members 14 each comprise a stem portion 15 attached at one end to the backing 11 and having radiused intersections 16 with the backing 11 on two sides to increase their breaking strengths at their junctures with the backing 11, and a head portion 17 at the end of the stem portion 15 opposite the backing 11. The sides of the head portion 17 are flush with the sides of the stem portion 15 on two opposite sides. The head portion 17 has parts projecting past the stem portion 15 on two opposite sides adjacent the radiused intersections 16 of the stem portions 15 with the backing 11, and has a rounded surface 18 opposite the stem portion 15 to help the head portion 17 enter between loops in a loop fastener portion. The head portion 17 also has transverse cylindrically concave surface portions 19 at the junctures between the stem portion 15 and the surfaces of the head portion 17 projecting over the backing 11, which concave surface portions 19 increase the head portion 17 break off strength at its juncture with the stem portion 15 and can help retain a loop under the head portion 17.

The hook members 14 are more easily and firmly engaged with many types of loop fastener portions than the hook members on known commercially available hook fastener portions, in large part because they are very small compared to the hook members on those commercially available hook fastener portions. Specifically, with reference to FIG. 2 showing a single representative one of the small hook members 14 on which its dimensions are represented by reference numerals between dimensional arrows, the hook members 14 each have a height dimension 20 from the upper surface 12 of less than 0.15 centimeter (0.06 inch) and preferably in the range of about 0.08 to 0.11 centimeter (0.03 to 0.043 inch). The stem and head portions 15 and 17 each have generally the same thickness dimension 21 of less than 0.046 centimeter (0.018 inch) and preferably in the range of 0.020 to 0.028 centimeter (0.008 to 0.012 inch) in a first direction parallel to the surfaces 12 and 13 of the backing 11. The stem portions 15 each have a width dimension 22 in the range of 0.018 to 0.03 centimeter (0.007 to 0.012 inch) in a second direction generally at a right angle to the first direction and parallel to the surfaces 12 and 13 of the backing 11, and the head portions 17 each have a width dimension 23 in the second direction that is between 0.007 and 0.038 centimeter (0.003 and 0.015 inch) greater than the width dimension 22 of the stem portion 15 and a total width of less than 0.1 centimeter and preferably in the range of 0.04 to 0.065 centimeter (0.016 to 0.026 inch).

While such small hook members 14 can easily penetrate between and engage loops even on inexpensive types of loop fastener portions, they individually have little holding power so that the hook fastener portion 10 includes at least 45, and preferably 70 to 100 hook members 14 per square centimeter (at least 300 and preferably 450 to 645 hook members per square inch) projecting from the upper surface 12 of the backing 11 to provide the desired holding power, while the total cross sectional area occupied by the head portions 17 in a plane parallel to the upper surface 12 of the backing 11 is less that 32 percent and preferably in the range of 5 to 15 percent of the area of the upper surface 12 so that the the large number of projecting hook members 14 can still be easily engaged with loop fastener portions.

Figure 3:
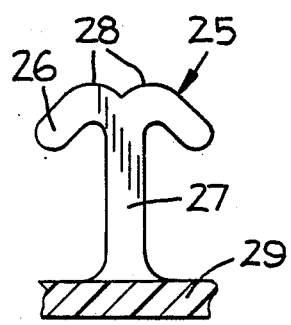
FIGS. 3 through 5 are enlarged fragmentary sectional views of alternate embodiments of hook portions that can be used in hook fastener portions according to the present invention.
Figure 4:
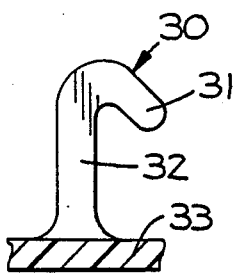
Figure 5:
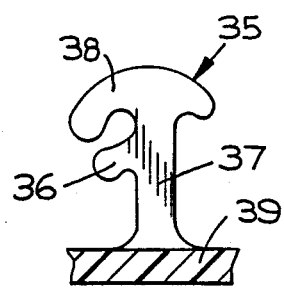

FIGS. 3 through 5 illustrate three of many alternate shapes that could be used for the hook members in alternate embodiments of hook fastener portions according to the present invention.

The hook member 25 illustrated in FIG. 3 differs from the hook member 14 in that its head portion 26 projects farther on opposite sides from its stem portion 27 and is generally uniformly thick so that it can more easily bend to engage with or disengage from loops on a loop fastener portion.

The hook member 30 illustrated in FIG. 4 differs from the hook member 14 in that its head portion 31 projects from only one side of its stem portion 32 and will thus cause significantly greater peel forces when peeled away from the direction the head portion 31 projects then when it is peeled toward the direction the head portion 31 projects.

The hook member 35 illustrated in FIG. 5 differs from the hook member 14 in that it includes a second side projection 36 from its stem portion 37 between its head portion 38 and a backing 39 to which it is attached, and will thus cause significantly greater peel forces when peeled away from the direction the second side projection projects then when it is peeled toward the direction the second side projection 36 projects.

Figure 6:
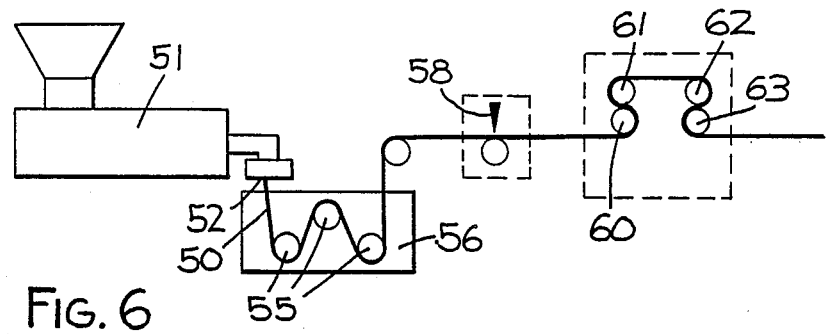
FIG. 6 schematically illustrates a method for making the hook fastener portion of FIG. 1.
Figures 7, 8:
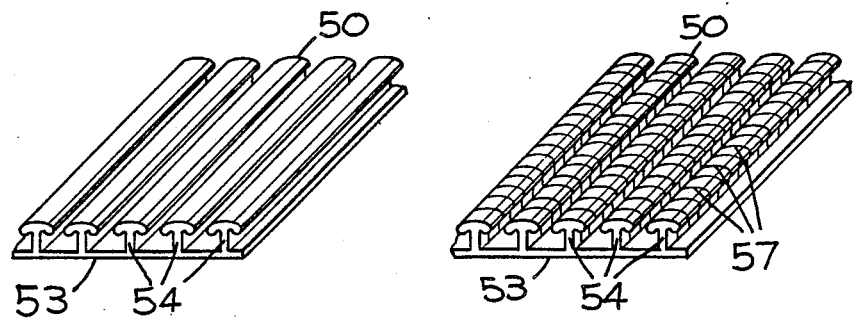
FIGS. 7 and 8 illustrate the structure of a strip at various stages of its processing in the method illustrated in FIG. 6.

The method for forming the hook fastener portion 10 is schematically illustrated in FIG. 6. Generally, that method includes first extruding a strip 50 shown in FIG. 7 of thermoplastic resin from an extruder 51 through a die 52 having an opening cut by electron discharge machining shaped to form the strip 50 with a base 53 and elongate spaced ribs 54 projecting above an upper surface of the base layer 53 that have the cross sectional shape of the hook portions to be formed. The strip 50 is pulled around rollers 55 through a quench tank 56 filled with a cooling liquid (e.g., water), after which the ribs 54 (but not the base layer 53) are transversely slit or cut at spaced locations along their lengths by a cutter 58 to form discrete portions 57 of the ribs 54 having lengths corresponding to the desired lengths of the hook portions to be formed as is shown in FIG. 8. The cutter 58 can cut using any conventional means such as reciprocating or rotating blades, lasers, or water jets, however preferably it cuts using reciprocating blades oriented at an angle of about 60 to 70 degrees with respect to length of the ribs 54 because of the greater resistance to deflection the ribs 54 have when cut from that angle rather than from an angle of 90 degrees with respect to the length of the ribs 54 which allows the very small and flexible ribs 54 to be cut.

After cutting of the ribs 54, the base 53 of the strip 50 is longitudinally stretched at a stretch ratio of at least 2 to 1, and preferably at a stretch ratio of about 4 to 1 between a first pair of nip rollers 60 and 61 and a second pair of nip rollers 62 and 63 driven at different surface speeds. Roller 61 is heated to heat the base 53 prior to stretching, and the roller 62 is chilled to stabilize the stretched base 53. Such stretching causes spaces between the portions 57 of the ribs 54 which then become the hook portions 14 for the completed hook fastener portion 10.

In making the hook fastener portion 10 described above, preferably the ribs 54 are spaced apart between their adjacent edges by at least about 0.50 millimeter, and preferably by between about 0.635 to 1.0 millimeter, and the stretching of the strip 50 will cause separation of the hook portions by at least about 0.50 millimeter, and preferably by between about 0.635 and 1.0 millimeter.

Figure 9:
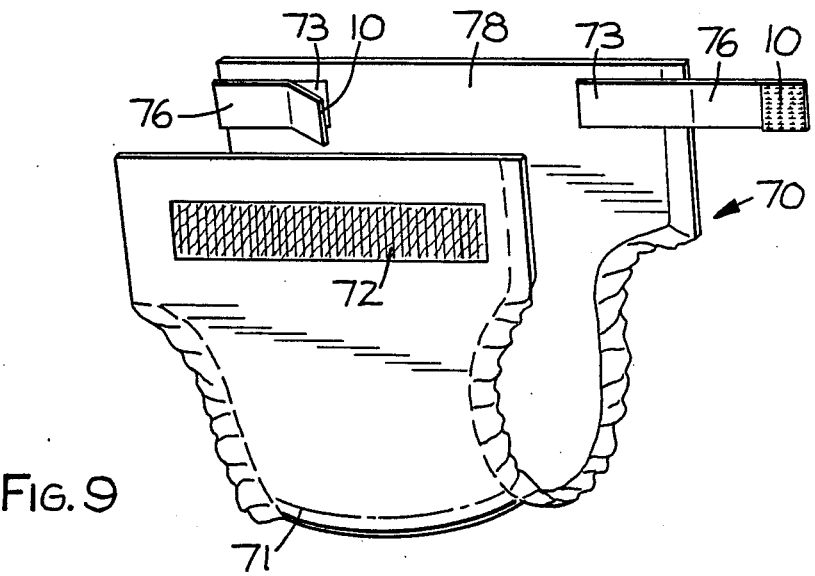
FIG. 9 is a perspective view of a disposable diaper including a hook fastener portion according to the present invention.

Referring now to FIG. 9 there is shown a disposable garment or diaper including two of the hook fastener portions 10 according to the present invention, which diaper is generally designated by the reference numeral 70. The diaper 70 and an outer liquid-impermeable polyolefin film 71 included in the diaper 70 are generally rectangular in shape, and the diaper 70 includes a loop fastener portion 72 across what is intended to be the front of the diaper 70, and the two hook fastener portions 10 adapted to engage end portions of the loop fastener portion 72 to hold the diaper 70 in place on a person wearing the diaper 70. The loop fastener portion 72 is elongate rectangular in shape (e.g., 20.3 centimeters long by 3.8 centimeters wide), is adhered by a bonding layer to the outer film 71 over its entire length along one of the shorter sides of the rectangular diaper 70 with its length parallel to the short edge of the diaper 70. The hook fastener portions 10 are supported on distal end portions of flexible elongate rectangular polymeric tabs 76 that have end portions 73 opposite the hook fastener portions 10 partly adhered both to inner edge portions of the outer film 71 and to an inner nonwoven polyolefin layer 78 of the diaper 70. The head portions on the hook like projections from the hook fastener portions 10 which are adapted to make releasable mechanical engagement with loops on the fastener portion 72 to afford attachment of the diaper 70 to a user such as an infant, are oriented so that the parts of the head portions that overhang the stem portions are aligned with the lengths of the tabs 76 so that the head portion will more securely engage the loops on the fastener portion 2. The tabs 76 may have layers of low tack pressure-sensitive adhesive on portions of their surfaces opposite the film 71 which allow the tabs 76 to be retained in a folded over condition (see the left tab 76 in FIG. 9) to protect the fastener portions 10 from chance unintentional engagement with various substrates prior to application of the diaper 70, at which time the tabs 76 may be easily peeled open (see the right tab 76 in FIG. 9) for engagement of the fastener portions 10 with end portions of the elongate fastener portion 72.

Example Hook Material

An example hook material from which hook fastener portions according to the present invention could be cut was made as described in this Example using the method described above with reference to FIG. 6.

A polypropylene/polyethylene random copolymer resin having a 4% polyethylene content and a melt flow index of 8.0 which is commercially available as WRS-6-166 from Shell Chemical Co., Houston, Tex. was extruded through a die shaped to produce a strip 50 having a base 53 and ribs 54 having the same cross sectional shape as the hook fastener portion 10 in said second direction by a 30 millimeter "Haake" extruder operated at a screw speed of 85 rpm to produce an output speed for the strip 50 from the die of 3 meters per minute. The extruded strip 50 was immediately quenched in a bath of cold (i.e., 15 degree Centigrade) water bath. The resulting strip 50 had an overall rib 54 width of 0.0635 centimeter, a thickness of the portion of the rib 54 that would become the stem portions of the hook members of 0.0254 centimeter, a rib height above the top surface of the backing of 0.1 centimeter, and a base 53 thickness of 0.028 centimeter. The ribs 54 were spaced center to center by 0.216 centimeter.

The ribs 54 of the strip 50 were slit in a transverse direction generally parallel to the base 53 at an angle of 64 degrees to their lengths at intervals of 0.024 centimeter by a reciprocating blade (i.e., a 10.12 cm wide stainless steel food blade available from American Safety Razor Co., Staunton, VA).

The base 53 of the strip 50 was then stretched between the heated roll 61 that had a surface temperature of 100 degrees Centigrade and a surface speed of 1.22 meters per minute, and the chilled roller 62 which had a surface speed of 8.88 meters per minute to provide a stretch ratio of 4 to 1. Stretching of the base 53 necked the strip 50 down in its transverse direction as it elongated the strip 50 in its longitudinal direction. The resulting strip 50 had a rib 54 height of 0.089 centimeter, a base 53 thickness of 0.0152 centimeter, a transverse center to center rib 54 spacing of 0.141 cm and a 0.0977 center to center machine directional stem spacing resulting in 73 hook members per square centimeter.

Pieces of the Sample Hook Material thus made (called "Sample Hook" hereafter) were then engaged with samples of a loop fastener portion commercially available as Style No. 19149 nylon 66 knitted loop material from Guilford Mills, Inc., Greensboro, NC, (called "Knitted Loop" hereafter) and the Dynamic Shear, T-Peel and Tensile Test properties of the engagement between those fastener portions were measured in accordance with the tests described below. Average results of those tests also shown in Table I, were a dynamic shear of 6.3 kilograms per centimeter (35.2 pounds per inch), a t-peel of 0.25 kilogram per centimeter (1.4 pounds per inch), and a tensile of 3.1 kilogram (6.8 pounds).

From our experience, it has been found that hook and loop fasteners for a disposable diaper closure should have a dynamic shear (i.e., the shear force required to separate the portions of the fastener by pulling them in opposite directions parallel to their backings that can be measured by a Dynamic Shear Test designated TM 1644, a copy of which together with copies of TM 1626 T-Peel Test, and TM 1259 Tensile Test are attached) of at least 1 kilogram per centimeter (3 pounds per inch) to ensure that the fastener will retain the diaper in place on a user; should resist a force peeling the fastener portions apart as measured by TM 1626 T-Peel Test, of at least 0.04 kilogram per centimeter (0.2 inch) and preferably greater than 0.1 kilogram per centimeter (0.5 pounds per inch) and no greater than 0.4 kilogram per centimeter (2 pounds per inch) to allow easy manual separation of the fastener portions by peeling them apart, and a tensile force (i.e., the force required to pull the fastener portions apart by applying the force at right angles to their backings as measured by TM 1259 Tensile Test) of greater than 1 and less than 4.5 kilograms (greater than 2.2 and less than 10 pounds) to ensure that the fastener portions initially firmly engage each other to provide immediate bond security upon engagement. Thus the test values for the Example Hook engaged with the Knitted Loop are all well within the acceptable range.

For the sake of comparison, we then engaged three different commercially available hook fastener portions with the Knitted Loop and performed the same Dynamic Shear, T-Peel and Tensile Tests. Those commercially available hook fastener portions were a molded hook fastener portion available as Style No. 932 from Aplix, Charlotte, N.C. (called "Molded Hook" hereafter); a hook fastener portion having a woven backing and projecting mushroom shaped hook portions available as Scotchmate Fastener Style No. SJ-3592 from 3M Company, St. Paul, Minn. (called "Woven Mushroom" hereafter); and a hook fastener portion having a woven backing and projecting hooks formed by slitting monofilament loops available as Scotchmate Fastener Style No. SJ-3402 from 3M Company, St. Paul, Minn.

(called "Woven Hook" hereafter). The results of those tests, reported in Table I, were for the Molded Hook/Knitted Loop a dynamic shear of 1.09 kilograms per centimeter (6.1 pounds per inch), a t-peel of 0.04 kilogram per centimeter (0.2 pounds per inch), and a tensile of 2.66 kilograms (5.9 pounds); for the Woven Mushroom/Knitted Loop a dynamic shear of 2.48 kilograms per centimeter (13.9 pounds per inch), a t-peel of 0.05 kilogram per centimeter (0.3 pounds per inch), and a tensile of 1.15 kilograms (2.5 pounds); and for the Woven Hook/Knitted Loop a dynamic shear of 0.79 kilograms per centimeter (4.4 pounds per inch), a t-peel of 0.05 kilogram per centimeter (0.3 pounds per inch), and a tensile of 1.64 kilograms (3.6 pounds). All of these values, like those for the Example material, were within the acceptable ranges set out above except for the Woven Hook which had an unacceptable dynamic shear value. In comparison to the other combinations, the Example Hook/Knitted Loop combination shows higher performance which is desired so that the size of the hook fastener portion can be minimized for any given application for further cost reductions.

An inexpensive nonwoven loop fastener portion (called "Nonwoven Loop" hereafter) was made as follows. Staple fibers (3.2 centimeter or 1¼ inch cut lengths of 4.75 denier crimped polyester) and binder fibers (3.2 centimeter or 1¼ inch cut lengths of 8 denier amorphous polyester) were blended at a ratio of 70% to 30% by weight, opened and fed to an even feeder that forms a fiber mat, and then processed in a roller top twin master card which constructed a nonwoven web having a basis weight of 0.10 kilogram per square meter (3 ounces per square yard). The web was then thermally set in a hot air oven to provide a lofty nonwoven fibrous structure with low web integrity or internal strength. The fibrous structure was then laminated to an ethylene vinyl acetate copolymer film having a thickness of 0.05 millimeter. The resulting laminate was bonded with heat and pressure in lines spaced every 0.508 centimeter which firmly anchored the fibers to the film along the bond lines.

The Example Hook, the Molded Hook, the Woven Mushroom, and the Woven Hook were then engaged with the inexpensive Nonwoven Loop and the same Dynamic Shear, T-Peel and Tensile Tests were performed. The results, reported in Table I, were for the Example Hook/Nonwoven Loop a dynamic shear of 1.97 kilograms per centimeter (11.0 pounds per inch), a t-peel of 0.21 kilogram per centimeter (1.2 pounds per inch), and a tensile of 1.83 kilograms (4.0 pounds); for the Molded Hook/Nonwoven Loop a dynamic shear of 0.18 kilograms per centimeter (1.0 pounds per inch), a t-peel of 0.03 kilogram per centimeter (0.2 pounds per inch), and a tensile of 0.47 kilograms (1.0 pounds); for the Woven Mushroom/Nonwoven Loop a dynamic shear of 1.44 kilograms per centimeter (8.1 pounds per inch), a t-peel of 0.05 kilogram per centimeter (0.3 pounds per inch), and a tensile of 0.67 kilograms (1.5 pounds); and for the Woven Hook/Nonwoven Loop a dynamic shear of 0.29 kilograms per centimeter (1.6 pounds per inch), a t-peel of 0.06 kilogram per centimeter (0.4 pounds per inch), and a tensile of 0.74 kilograms (1.6 pounds). As can be seen from these test values, the Example Hook can make acceptable engagement with the Nonwoven loop, whereas the Molded Hook, the Woven Mushroom, and the Woven Hook all failed to meet the performance criteria in at least one of the tests.

TABLE I

| Hook and Loop Fastener Portions Engaged | Dynamic Shear (kg/cm) | T.Peel (kg/cm) | Tensile (kg) |
| --- | --- | --- | --- |
| Acceptable Value Range | >1.0 | 0.04 to 0.4 | 1 to 4.5 |
| Example Hook/Knitted Loop | 6.3 | 0.25 | 3.08 |
| Molded Hook/Knitted Loop | 1.09 | 0.04 | 2.66 |
| Woven Mushroom/Knitted Loop | 2.48 | 0.05 | 1.15 |
| Woven Hook/Knitted Loop | 0.70 | 0.05 | 1.64 |
| Example Hook/Nonwoven Loop | 1.79 | 0.21 | 1.83 |
| Molded Hook/Nonwoven Loop | 0.18 | 0.03 | 0.47 |
| Woven Mushroom/Nonwoven Loop | 1.44 | 0.05 | 0.67 |
| Woven Hook/Nonwoven Loop | 0.29 | 0.06 | 0.74 |

The present invention has now been described with reference to several embodiments thereof. It will be apparent to those skilled in the art that many changes can be made in the embodiments described without departing from the scope of the present invention. For example, many other shapes for the hook members within the size and population limitations indicated may be envisioned. Additionally, Diapers or other disposable garments may have hook fastener portions attached thereon in many other locations than that illustrated, and the loop fastener portions the hook fastener portions engage may be layers (e.g., nonwoven layers) incorporated in the diaper or garment for other purposes such as padding or absorption. Thus the scope of the present invention should not be limited to the structures described in this application, but only by structures described by the language of the claims and the equivalents of those structures.

I claim:

1. A disposable garment or diaper including a flexible laminate adapted to be applied around a portion of an individual, and hook and loop fastener means for fastening together spaced portions of said laminate to secure said garment or diaper to the individual, said fastener means including at least one loop fastener portion defining loops attached to one of said portions, and at least one unitary hook fastener portion of a resiliently flexible, polymeric resin comprising a base having generally parallel upper and lower major surfaces with said lower surface fastened to a different one of said portions of said laminate, and at least 45 spaced hook members per square centimeter projecting at generally a right angle from the upper surface of said base and adapted to releasably engage the loops of said loop fastener portion, said hook members having a height from said upper surface of less than 1.5 millimeter and each comprising a stem portion attached at one end to said base, and a head portion at the end of said stem portion opposite said base, which head portion has a rounded surface opposite said stem portion, said stem and head portions having generally the same thickness of less than 0.046 centimeter in a first direction parallel to the surfaces of said backing said stem portion having a width in the range of 0.018 to 0.03 centimeter in a second direction generally at a right angle to said first direction and parallel to the surfaces of said backing and said head portion having a width at least 0.007 centimeter greater than said stem portion and a total width of less than about 0.1 centimeter in said second direction, the total cross sectional area of said head portions in a plane parallel to said upper surface being less than 32 percent of the area of said upper surface.

2. A disposable garment or diaper according to claim 1 wherein the maximum total cross sectional area of said head portions in a plane parallel to said upper surface is in the range of 5 to 15 percent of the area of said upper surface.

3. A disposable garment or diaper according to claim 1 having in the range of 70 to 100 spaced hook members per square centimeter projecting at generally a right angle from the upper surface of said base.

4. A disposable garment or diaper according to claim 1 wherein said polymeric material is a thermoplastic resin and said hook members have an elastic modulus in the range of 100 to 500 megaPascals measured according to ASTM D 882-80a in said second direction.

5. A disposable garment or diaper according to claim 1 wherein said base has a generally uniform thickness between said upper and lower surfaces of between 0.05 millimeter and 0.4 millimeters.

6. A disposable garment or diaper according to claim 1 wherein said hook members have a height from said upper surface of about 0.08 to 0.11 centimeter.

7. A disposable garment or diaper according to claim 1 wherein said loop fastener portion is of nonwoven material.

8. A unitary hook fastener portion of a resiliently flexible, polymeric resin comprising a base having generally parallel upper and lower major surfaces, and at least 45 spaced hook members per square centimeter projecting at generally a right angle from the upper surface of said base, said hook members having a height from said upper surface of less than 1.5 millimeter and each comprising a stem portion attached at one end to said base, and a head portion at the end of said stem portion opposite said base, which head portion has a rounded surface opposite said stem portion, said stem and head portions having generally the same thickness of less than 0.046 centimeter in a first direction parallel to the surfaces of said backing, said stem portion having a width in the range of 0.018 to 0.03 centimeter in a second direction generally at a right angle to said first direction and parallel to the surfaces of said backing, and said head portion having a width at least 0.007 centimeter greater than said stem portion and a total width of less than about 0.1 centimeter in said second direction, the total cross sectional area of said head portions in a plane parallel to said upper surface being less than 32 percent of the area of said upper surface.

9. A unitary hook fastener portion according to claim 8 wherein the maximum total cross sectional area of said head portions in a plane parallel to said upper surface is in the range of 5 to 15 percent of the area of said upper surface.

10. A unitary hook fastener portion according to claim 8 having in the range of 70 to 100 spaced hook members per square centimeter projecting at generally a right angle from the upper surface of said base.

11. A unitary hook fastener portion according to claim 8 wherein said polymeric material is a thermoplastic resin and said hook members have an elastic modulus in the range of 100 to 500 megaPascals measured according to ASTM D 882-80a in said second direction.

12. A unitary hook fastener portion according to claim 8 wherein said base has a generally uniform thickness between said upper and lower surfaces of between 0.05 millimeter and 0.4 millimeters.

13. A unitary hook fastener portion according to claim 8 wherein said hook members have a height from said upper surface of about 0.08 to 0.11 centimeter.

* * * * *